United States Patent [19]

Perrior et al.

[11] Patent Number: 5,039,807
[45] Date of Patent: Aug. 13, 1991

[54] PHENYL PYRID(-ONE OR-THIONE) COMPOUNDS WHICH ARE INTERMEDIATES

[75] Inventors: Trevor R. Perrior, Wokingham; David J. Tapolczay, Bracknell, both of England

[73] Assignee: Imperial Chemical Industries PLC, London, England

[21] Appl. No.: 327,135

[22] Filed: Mar. 22, 1989

Related U.S. Application Data

[62] Division of Ser. No. 89,823, Aug. 27, 1987, Pat. No. 4,866,078.

[30] Foreign Application Priority Data

Sep. 3, 1986 [GB] United Kingdom ............... 8621217

[51] Int. Cl.$^5$ ..................................... C07D 211/72
[52] U.S. Cl. ................................ 546/288; 546/290; 546/297; 546/298; 546/300; 546/301; 546/303; 546/296
[58] Field of Search ............... 546/286, 288, 290, 297, 546/298, 303, 296, 300, 301

[56] References Cited

U.S. PATENT DOCUMENTS 3,721,676 3/1973 Witzel et al. .................... 546/290

OTHER PUBLICATIONS

Chemical Abstracts, vol. 72; No. 4, Abstract 21616g, p. 308, Jan. 26, 1970.
Becher, J. of Heterocyclic Chemistry, vol. 21; No. 1, pp. 41–48, 1984.

*Primary Examiner*—C. Warren Ivy
*Assistant Examiner*—Zinna Northington-Davis
*Attorney, Agent, or Firm*—Cushman, Darby & Cushman

[57] ABSTRACT

A compound of formula (I)

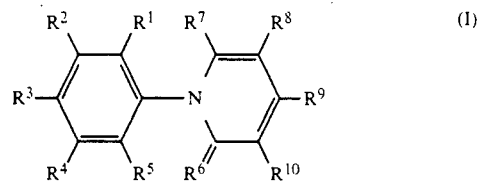

wherein
$R^1$, $R^2$, $R^4$ and $R^5$ are independently selected from hydrogen, halogen, lower alkyl optionally substituted by halogen, lower alkoxy optionally substituted by halogen and lower alkenyl optionally substituted by halogen;
$R^3$ is halogen, amino, mono- or di(lower alkyl)-amino, lower alkyl substituted by halogen, lower alkoxy optionally substituted by halogen and lower alkenyl optionally substituted by halogen provided that $R^3$ is not monochloro or monobromo-methyl;
$R^6$ is oxygen or sulphur;
$R^7$ and $R^{10}$ are independently selected from hydrogen, halogen, lower alkyl optionally substituted by halogen, lower alkoxy optionally substituted by halogen, and lower thioalkoxy optionally substituted by halogen; and
$R^8$ is hydrogen, halogen, optionally substituted lower alkyl, optionally substituted lower alkoxy, optionally substituted lower thioalkoxy, cyano, nitro, optionally substituted oximino, optionally substituted lower alkenyl, optionally substituted aryloxy, optionally substituted amino or $S(O)nR^{11}$ wherein n is 0, 1 or 2 and $R^{11}$ is optionally substituted lower alkyl;
$R^9$ is hydrogen, or lower alkyl optionally substituted by halogen, lower alkenyl optionally substituted by halogen or $CO_2R^{12}$ wherein $R^{12}$ is lower alkyl optionally substituted by halogen; provided that $R^1$, $R^2$, $R^3$, $R^4$ and $R^5$ are not all hydrogen; and further provided that when $R^3$ is trifluoromethyl and $R^1$ and $R^5$ are halogen, $R^2$ and $R^4$ are not both hydrogen, or $R^7$, $R^8$, $R^9$ and $R^{10}$ do not comprise from one to four halogen or trihalomethyl substitutents.

2 Claims, No Drawings

PHENYL PYRID(-ONE OR-THIONE) COMPOUNDS WHICH ARE INTERMEDIATES

This is a divisional of U.S. application Ser. No. 07/089,823, filed Aug. 27, 1987, now U.S. Pat. No. 4,866,078, issued Sept. 12, 1989.

This invention relates to novel aryl pyridones useful as insecticidal agents.

The invention provides a compound of formula (I)

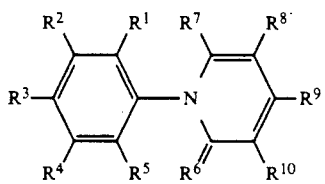

wherein
$R^1$, $R^2$, $R^4$ and $R^5$ are independently selected from hydrogen, halogen, lower alkyl optionally substituted by halogen, lower alkoxy optionally substituted by halogen and lower alkenyl optionally substituted by halogen;

$R^3$ is halogen, amino, mono- or di-(lower alkyl)-amino, lower alkyl substituted by halogen, lower alkoxy optionally substituted by halogen and lower alkenyl optionally substituted by halogen provided that $R^3$ is not monochloro or monobromo-methyl;

$R^6$ is oxygen or sulphur;

$R^7$ and $R^{10}$ are independently selected from hydrogen, halogen, lower alkyl optionally substituted by halogen, lower alkoxy optionally substituted by halogen, and lower thioalkoxy optionally substituted by halogen; and $R^8$ is hydrogen, halogen, optionally substituted lower alkyl, optionally substituted lower alkoxy, optionally substituted lower thioalkoxy, cyano, nitro, optionally substituted oximino, optionally substituted lower alkenyl, optionally substituted aryloxy, optionally substituted amino or $S(O)nR^{11}$ wherein n is 0, 1 or 2 and $R^{11}$ is optionally substituted lower alkyl;

$R^9$ is hydrogen, or lower alkyl optionally substituted by halogen, lower alkenyl optionally substituted by halogen or $CO_2R^{12}$ wherein $R^{12}$ is lower alkyl optionally substituted by halogen; provided that $R^1$, $R^2$, $R^3$, $R^4$ and $R^5$ are not all hydrogen; and further provided that when $R^3$ is trifluoromethyl and $R^1$ and $R^5$ are halogen, $R^2$ and $R^4$ are not both hydrogen, or $R^7$, $R^8$, $R^9$ and $R^{10}$ do not comprise from one to four halogen or trihalomethyl substitutents.

As used herein the term "lower" used in relation to alkyl or alkoxy groups means groups having from 1 to 6 carbon atoms preferably from 1 to to 3 carbon atoms and when used in relation to alkenyl groups means groups having from 2 to 6 carbon atoms, preferably 2 or 3 carbon atoms. The term "aryl" includes phenyl.

Suitably $R^1$, $R^2$, $R^3$, $R^4$ and $R^5$ are selected from hydrogen, halogen such as fluorine, chlorine or bromine; lower alkyl such as methyl or ethyl, lower alkoxy, such as methoxy or halo(lower)alkyl such as trifluoromethyl.

Preferred examples of $R^1$ and $R^5$ include hydrogen, fluorine, chlorine and bromine.

Preferably both $R^1$ and $R^5$ are chlorine.

Preferred examples of $R^2$ and $R^4$ include hydrogen, halogen in particular, fluorine, lower alkyl such as methyl or ethyl and lower alkoxy such as methoxy.

Preferred examples of $R^3$ include halogen such as fluorine and chlorine, amino and halo lower alkyl such as trifluoromethyl.

Preferably $R^6$ is oxygen.

Examples of suitable halogen atoms for $R^7$, $R^8$ and $R^{10}$ include bromo.

Preferably $R^7$ and $R^{10}$ are both hydrogen.

Examples of $R^8$ include hydrogen, halo, lower alkyl optionally substituted by halo or hydroxy; cyano; nitro; oximino optionally substituted by lower alkyl, aryl, lower alkenyl or aralkyl wherein the aryl portion is optionally substituted with halogen or nitro; lower alkenyl optionally substituted by halogen or cyano; amino; or $S(O)R^{11}$ wherein n is 0, 1, or 2 and $R^{11}$ is lower alkyl optionally substituted by halogen such as fluorine.

Specific examples of $R^8$ include hydrogen, iodo, methyl, hydroxymethyl, chloromethyl, difluoromethyl, dichloromethyl, thiomethyl, ethoxyimino, t-butyloximino, p-nitrobenzyloxyimino, phenoxyimino, pentafluorobenzyloximino, prop-2-enyloxyimino, 2,2-dichloroethenyl, 2-cyanoethenyl, ethynyl or $S(O)CF_3$.

Preferably $R^8$ is hydrogen or cyano.

Suitable groups $R^9$ include halo(lower)alkyl, branched chain lower alkyl, halo(lower)alkenyl, or a lower carboxylic ester group.

Examples of suitable groups $R^9$ include trifluoromethyl, 2,2-di-bromoethenyl, ethoxycarbonyl and tert-butyl.

Specific examples of compounds of formula I are set out in Table I.

TABLE I

| COMPOUND | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 1 | Cl | H | $CF_3$ | H | Cl | O | H | H | $CO_2Et$ | H |
| 2 | Cl | H | $CF_3$ | H | Cl | O | H | H | $CHCBr_2$ | H |
| 3 | H | H | $CF_3$ | H | H | O | H | H | $CF_3$ | H |
| 4 | Cl | H | $CF_3$ | $CH_3$ | Cl | O | H | H | $CF_3$ | H |
| 5 | Cl | H | $CF_3$ | $C_2H_5$ | Cl | O | H | H | $CF_3$ | H |
| 6 | F | F | $CF_3$ | $OCH_3$ | F | O | H | H | $CF_3$ | H |
| 7 | F | F | $CF_3$ | F | F | O | H | H | $CF_3$ | H |
| 8 | F | F | F | F | F | O | H | H | $CF_3$ | H |
| 9 | F | H | $CF_3$ | H | $OCH_3$ | O | H | H | $CF_3$ | H |
| 10 | Cl | H | $CF_3$ | H | $OCH_3$ | O | H | H | $CF_3$ | H |
| 11 | F | H | $CF_3$ | H | F | O | H | H | $tC_4H_9$ | H |
| 12 | Cl | H | $CF_3$ | H | Cl | O | H | H | $CHF_2$ | H |
| 13 | Cl | H | $CHF_2$ | H | Cl | O | H | H | $CF_3$ | H |
| 14 | Cl | H | $CHCl_2$ | H | Cl | O | H | H | $CF_3$ | H |
| 15 | Cl | H | $CF_3$ | H | Cl | O | H | $SCF_3$ | $CF_3$ | H |
| 16 | Cl | H | $CF_3$ | H | Cl | O | H | $(CH_2)_3CH_3$ | $CF_3$ | H |
| 17 | Cl | H | $CF_3$ | H | Cl | O | H | H<br>—CH=N—OCH$_2$CH$_3$ | $CF_3$ | H |

TABLE I-continued

| COMPOUND | R$^1$ | R$^2$ | R$^3$ | R$^4$ | R$^5$ | R$^6$ | R$^7$ | R$^8$ | R$^9$ | R$^{10}$ |
|---|---|---|---|---|---|---|---|---|---|---|
| 18 | Cl | H | CF$_3$ | H | Cl | O | H | $-$C=NOCH$_2$C$_5$H$_6$ (H) | CF$_3$ | H |
| 19 | Cl | H | CF$_3$ | H | Cl | O | H | $-$C=N$-$OCH$_2-$C$_6$H$_4-$NO$_2$ | CF$_3$ | H |
| 20 | Cl | H | CF$_3$ | H | Cl | O | H | $-$C=N$-$OCH$_3$ | CF$_3$ | H |
| 21 | Cl | H | CF$_3$ | H | Cl | O | H | $-$C=N$-$O$-$C$_6$H$_5$ | CF$_3$ | H |
| 22 | Cl | H | CF$_3$ | H | Cl | O | H | $-$C=N$-$O$-$C(CH$_3$)$_3$ | CF$_3$ | H |
| 23 | Cl | H | CF$_3$ | H | Cl | O | H | $-$C=N$-$OCH$_2$CH=CH$_2$ | CF$_3$ | H |
| 24 | Cl | H | CF$_3$ | H | Cl | O | H | $-$C=N$-$OCH$_2-$C$_6$F$_5$ | CF$_3$ | H |
| 25 | Cl | H | CF$_3$ | H | Cl | O | H | CH$_3$ | CF$_3$ | H |
| 26 | Cl | H | CF$_3$ | H | Cl | O | H | $-$S(O)CF$_3$ | CF$_3$ | H |
| 27 | Cl | H | CF$_3$ | H | Cl | O | H | $-$CH=CCl$_2$ | CF$_3$ | H |
| 28 | Cl | H | CF$_3$ | H | Cl | O | H | $-$SCH$_3$ | CF$_3$ | H |
| 29 | Cl | H | CF$_3$ | H | Cl | O | H | $-$CN | CF$_3$ | H |
| 30 | Br | H | CF$_3$ | H | Br | O | H | CN | CF$_3$ | H |
| 31 | Cl | H | CF$_3$ | H | Cl | O | H | NO$_2$ | CF$_3$ | H |
| 32 | Cl | H | CF$_3$ | H | Cl | O | H | CH$_2$OH | CF$_3$ | H |
| 33 | Cl | H | CF$_3$ | H | Cl | O | H | CH$_2$Cl | CF$_3$ | H |
| 34 | Cl | H | CF$_3$ | H | Cl | O | H | $-$C≡CH | CF$_3$ | H |
| 35 | Cl | H | CF$_3$ | H | Cl | O | H | $-$CHF$_2$ | CF$_3$ | H |
| 36 | Cl | H | CF$_3$ | H | Cl | O | H | $-$CHCl$_2$ | CF$_3$ | H |
| 37 | Cl | H | CF$_3$ | H | Cl | O | H | CH=CHCN | CF$_3$ | H |
| 38 | Cl | H | NH$_2$ | H | Cl | O | H | H | CF$_3$ | H |
| 39 | Cl | H | Cl | H | Cl | O | H | H | CF$_3$ | H |
| 40 | Cl | H | CH$_2$F | H | Cl | O | H | H | CF$_3$ | H |
| 41 | Cl | H | (CH$_3$)$_2$CF | H | Cl | O | H | H | CF$_3$ | H |

The compounds of formula I may be prepared by reacting a compound of formula (II):

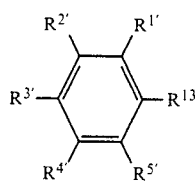

(II)

wherein
R$^{1'}$, R$^{2'}$, R$^{3'}$, R$^{4'}$ and R$^{5'}$ are equivalent to R$^1$, R$^2$, R$^3$, R$^4$ and R$^5$ respectively as hereinbefore defined or a precursor thereof and R$^{13}$ is a leaving group such as halo, with a compound of formula (III):

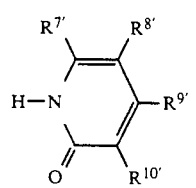

(III)

where R$^{7'}$, R$^{8'}$, R$^{9'}$ and R$^{10'}$ are equivalent to R$^7$, R$^8$, R$^9$ and R$^{10}$ respectively as hereinbefore defined or a precursor thereof and thereafter if necessary carrying out one or more of the following steps:
(i) converting a group R$^{1'}$, R$^{2'}$, R$^{3'}$, R$^{4'}$, R$^{5'}$, R$^{7'}$, R$^{8'}$, R$^{9'}$, R$^{10'}$ to R$^1$, R$^2$, R$^3$, R$^4$, R$^5$, R$^7$, R$^8$, R$^9$ or R$^{10}$ respectively; or (ii) converting the carbonyl group to =S.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, an alcohol or an aprotic polar solvent such as dimethylformamide or dimethylacetamide. Suitable halo groups R$^{13}$ include fluoro, chloro, bromo or iodo and if necessary an appropriate catalyst such as a crown ether or copper can be added depending upon the precise nature of R$^{13}$. Further details of the processes for preparation of the compounds may be ascertained from the Examples set out hereinafter.

Optional step (ii) above may be carried out by reacting compounds of formula (I) wherein R$^6$ is oxygen with a thiolating agent such as phosphorus pentasulphide. The reaction is suitably carried out in an organic solvent such as pyridine at elevated temperatures of from 50° C. to 150°.

As used herein the term "precursor" applies to a group which can be converted to a chemical group R$^1$, R$^2$, R$^3$, R$^4$, R$^5$, R$^7$, R$^8$, R$^9$ or R$^{10}$ by standard chemical techniques. A particularly useful precursor of this type is the formyl group as R$^{8'}$ or R$^{9'}$. This group can be converted to various oxime, optionally substituted alkyl, optionally substituted alkenyl, optionally substituted alkynyl, and cyano groups R$^8$ as illustrated hereinafter.

For example compounds of formula (I) where R$^9$ is optionally substituted alkenyl can be prepared by reacting a compound of formula (IV)

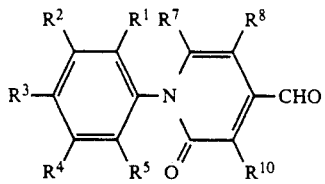 (IV)

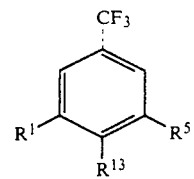 (VI)

wherein $R^1$, $R^2$, $R^3$, $R^4$, $R^5$, $R^7$, $R^8$ and $R^{10}$ are as hereinbefore defined with an appropriate substituted alkane in the presence of zinc and triphenyl phosphine under conventional Wittig reaction conditions.

An additional useful precursor of this type is the nitro group, in particular as $R^{3'}$ as this can be converted to amino as illustrated hereinafter.

A further useful precursor group, particularly for the $R^{3'}$ group is ethoxycarobnyl. This group can be readily converted to various hydroxy alkyl groups such as hydroxy methyl or 1-methyl-1-hydroxy ethyl by standard techniques such as by reduction or using Grignard reactions. The hydroxy alkyl groups can be converted directly to compounds of the invention, for example by halogenation or they may be converted to a second precursor such as formyl which is discussed above.

Descriptions of reactions using these precursors is given by way of illustration in the Examples hereinafter.

Intermediates of formula (V)

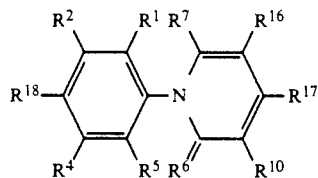 (V)

where $R^1$, $R^2$, $R^3$, $R^4$, $R^5$, $R^7$ and $R^{10}$ are as defined in relation to formula (I), $R^{16}$ and $R^{17}$ are selected from $R^8$ and $R^{10}$ respectively or formyl and $R^{18}$ is $R^3$ is hereinbefore defined, nitro or $C_{1-6}$ alkoxycarbonyl or lower alkyl substituted by hydroxy provided that at least one of $R^{16}$, $R^{17}$ and $R^{18}$ is not $R^8$, $R^{10}$ or $R^3$ respectively are novel and as such form an aspect of the invention.

Compounds of formula (I) can be converted to other compounds of formula (I) having different substituent R groups by conventional methods if desired. For example, when one of $R^1$, $R^2$, $R^3$, $R^4$ or $R^5$ is fluoro, it can be converted to an alkoxy group by reaction with an appropriate alkoxy anion of formula $R^{14}O^-$ where $R^{14}$ is lower alkyl. Anions of formula $R^{14}O^-$ may be prepared by dissolving sodium metal in an alcohol of formula $R^{14}OH$ suitably at moderate temperatures of from 0° to 100° C., preferably at room temperature.

Compounds of formula (II) are largely known compounds or they can be produced from known compounds by conventional methods. However compounds of formula (II) where $R^3$ is trifluoromethyl and $R^2$ or $R^4$ is lower alkyl optionally substituted by halogen are novel and as such form part of the invention.

These compounds can be prepared by reacting a compound of formula (VI)

wherein $R^1$, $R^5$ and $R^{13}$ are as hereinbefore defined with a compound of formula $R^{15}$-$R^{16}$ where $R^{15}$ is a lower alkyl group and $R^{16}$ is halogen such as iodine in the presence of a base such as n-butyl lithium.

Compounds of formula (IV) can be prepared by oxidation of a compound of formula (VII)

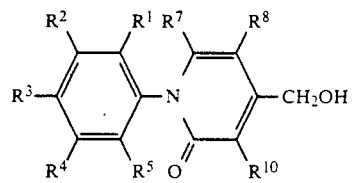 (VII)

wherein $R^1$, $R^2$, $R^3$, $R^4$, $R^5$, $R^7$, $R^8$ and $R^{10}$ are as hereinbefore defined. The oxidation is suitably carried out using an oxidising agent for example using Swern oxidation procedures. The reaction is suitably carried out in an organic solvent such as dichloromethane in the presence of a base low temperatures for example of from $-100°$ C. to 0° C. are suitably employed.

Compounds of formula (VII) can be prepared by reduction of a compound of formula (I) wherein $R^9$ is $CO_2R^{12}$ using a reducing agent such as lithium borohydride. The reaction is suitably carried out in an inert organic solvent such as tetrahydrofuran at temperatures of form 0°-150° C.

Certain compounds of formula (III) are also novel and these also form part of the invention. Therefore in a further aspect of the invention there is provided a compound of formula (IIIA):

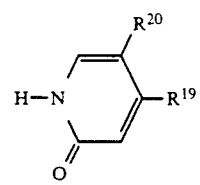 (IIIA)

wherein $R^{19}$ is trihalomethyl and $R^{20}$ is an electrophilic group $R^{8'}$ as hereinbefore defined.

Particular examples of $R^{19}$ includes trifluoromethyl.

Particular examples of $R^{20}$ include nitro, lower thioalkoxy optionally substituted by halogen such as trifluoromethylthio, formyl, and lower alkyl as methyl or butyl optionally substituted by halogen.

Compounds of formula (IIIA) wherein $R^{20}$ is an electrophilic group other than nitro can be prepared by reacting a compound of formula (VIII)

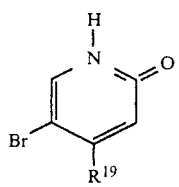

wherein R$^{19}$ is as hereinbefore defined with a base and a compound $$R^{20}-R^{21}$$

wherein R$^{21}$ is a leaving group such as halogen. Examples of such reactions are given hereinafter.

The base used in the reaction is preferably a combination of sodium hydride followed by t-butyllithium. Suitably 2 equivalents of base are employed. The reaction is preferably carried out in an inert organic solvent such as tetrahydrofuran.

Compounds of formula (IIIA) wherein R$^{18}$ is nitro can be prepared by nitration of a compound of formula (VIII) under standard conditions.

Other compounds of formula (III) and compounds of formula (VIII) are either known compounds or they can be produced from known compounds by conventional methods.

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products), horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl creson. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be sued. For agricultural or horticultural purposes, an aqueous preparation containing between 0.0001% and 0.1% by weight of the active ingredient (approximately equivalent to from 5-2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:
a) Pyrethroids such as permethrin, esfenvalerate, deltamethrin, cyhalothrin in particular cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;
b) Organophosphates such as profenofos, sulprofos, methyl parathion, azinphos-methyl, demoton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphosmethyl, fenitrothion or diazionon;
c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;
d) Benzoyl ureas such as triflumeron, or chlorofluazuron;
e) Organic tin compounds such as cyhexatin, fenbutatin oxide, azocyclotin;
f) Macrolides such as avermectins or milbemyins, for example such as avamectin, avermectin, and milbemycin;
g) Hormones such as pheromones;
h) Organochlorine compounds such as benzene hexachloride, DDT, chlordane or dieldrin.
i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chofentezine, flubenzimine, hexythiazox and tetradifon, moltilicides such as dicofol on propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamax, and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compounds of formula I and compositions comprising them have shown themselves active against a variety of insect and other invertebrate pests. They are particularly useful in controlling public health pests such as flies and cockroaches. Certain compounds of formula (I) and compositions comprising them are useful against pests in rice crops, such as rice hoppers. They may also be active against organophosphate and pyrrethroid resistant strains of pests such as houseflies (*Musca domestica*). They may be effective in combating both susceptible and resistant strains of the pests in their adult, larval and intermediate stages of growth, and may be applied to the infested host animal by topical, oral or parenteral administration. The compounds also have nematocidal activity.

The following Examples illustrate various aspects of this invention. In the Preparations and Examples the products were usually identified and characterised by means of nuclear magnetic resonance spectroscopy and infra red spectroscopy. In each case where a product is specifically named its spectral characteristics are consistent with the assigned structure.

EXAMPLE 1

This Example illustrates the preparation of 4-ethoxy carbonyl-1-(2,6-dichloro-4-trifluoromethyl-phenyl)-2-pyridone (Compound 1 in Table I).

Sodium hydride (10.7 g of a 50% dispersion in mineral oil, 0.23 mol) was washed with diethyl ether in a dry flask flushed with nitrogen. Dimethyl formamide (110 ml) was added and the mixture gently stirred at room temperature whilst 4-carboethoxy-2-pyridone (35.1 g, 0.21 mol) was added portionwise, being rinsed into the flask with a further volume of dimethylformamide (20 ml).

After 15 minutes, when gas evolution had ceased, 3,5-dichloro-4-fluoro benzotrifluoride (100 g, 0.43 mol) was added, the reaction was heated at 90° C. for 3-5 hours and left to stand at room temperature for 16 hours.

A few drops of ethanol were added and the mixture stirred for five minutes before being poured into water (1000 ml) and extracted with ethyl acetate. The extract was well washed with water, dried over magnesium sulphate and evaporated in vacuo. The residue was washed with an ethyl acetate/petrol mixture to give the required compound (30 g) which could be purified further by recrystallization from a mixture of ethyl acetate and petrol to give white crystals (mp 135.7°-137.3° C.); δ (d$_6$-acetone) 8.0 (2H,s), 7.6 (1H,d), 7.2 (1H,d), 6.8 (1H,dd), 4.4 (2H,q), 1.4 (3H,t).

EXAMPLE 2

This example illustrates the preparation of 4-(2,2-dibromovinyl)-1-(2,6-dichloro-4-trifluoro-methyl-phenyl)-2-pyridone (Compound 2).

To lithium borohydride (0.32 g, 14.5 mmol) suspended in tetrahydrofuran (10 ml) was added a solution of 4-ethoxy carbonyl-1-2,6 dichloro-4-trifluoromethyl-phenyl)-2-pyridone (Compound 1, 10 g, 26 mmol) in tetrahydrofuran (30 ml). The mixture was heated under reflux for two hours, allowed to cool to room temperature and the solvent removed in vacuo. The residue was shaken with water and ethyl acetate, the layers separated, and the aqueous layer extracted with ethyl acetate. The combined organic layers were washed with water, then brine, dried over magnesium sulphate and evaporated in vacuo to give 4-hydroxymethyl-1-(2,6-dichloro-4-trifluoromethyl-phenyl)-2-pyridone as a brown gum (9.2 g) (Compound 13).

The material was not further purified, but dissolved in dichloromethane (30 ml) and used in the next step.

A well-stirred solution of oxalyl chloride (3 ml, 32.5 mmol) in dichloromethane (75 ml) was cooled to −60° C. in a dry flask under nitrogen.

A solution of dimethylsulphoxide (5 ml, 65 mmol) in dichloromethane was rapidly added, keeping the reaction temperature below −50° C. After two minutes the dichloromethane solution of alcohol (13) was added over five minutes, and the reaction stirred at −50° to −60° C. for fifteen minutes. Triethylamine (35 ml, 0.25 mol) was then added and after a further five minutes the cooling bath was removed and the reaction mixture allowed to warm to room temperature. The reaction mixture was poured into water, the layers separated and the aqueous layer extracted with dichloromethane. The combined organic layers were washed sequentially with brine 1% hydrochloric acid, 5% sodium carbonate and water and dried with magnesium sulphate.

The solvent was evaporated in vacuo and the residue chromatographed on silica with 40% diethyl ether in petrol as eluent to afford 1-(2,6-dichloro-4-trifluoromethylphenyl)-4-formyl-2-pyridone as a white solid (5.1 g, mp 114.8°–116.7° C.); $\delta$ ($d_6$-acetone) 10.05 (1H,s), 8.1 (2H,s), 7.7 (1H,d), 7.2 (1H,s), 6.75 (1H,d). The aldehyde (1 g, 3 mmol) was added in one portion to a well-stirred mixture of carbon tetrabromide (1.97 g, 6 mmol), triphenylphosphine (1.56 g, 6 mmol) and zinc powder (0.39 g, 6 mmol) in dichloromethane (20 ml) which had been pre-stirred for two minutes. The reaction mixture was heated under reflux for one hour, cooled to room temperature, and poured into water. The organic layers were washed with water, then brine and dried over magnesium sulphate.

Evaporation in vacuo gave a brown residue which was treated with diethyl ether, filtered and the filtrate purified by column chromatography on silica with 1:1 by the careful addition of water (50 ml) and allowed to warm to room temperature. The mixture was poured into water (350 ml) and extracted with ether (2×300 ml). The organic layers were washed well with water, dried over magnesium sulphate and the solvent evaporated in vacuo. The resulting liquid was distilled in a Kugelrohr apparatus to give the required compound (3.7 g mp 70° C. at 20 mm Hg); $\delta$ ($CDCl_3$) 7.6 (1H,d), 2.5 (3H,s).

EXAMPLE 5

3,5-dichloro-2-ethyl-4-fluoro benzotrifluoride was prepared by the method described in Example 4 using ethyl iodide in place of methyl iodide.

EXAMPLE 6

The following compounds were prepared by the method described in Example 1 from the appropriate compounds of the formula I (Hal represents fluoro) and formula II.

(i) 1-(2,6-dichloro-4-trifluoromethyl-3-methyl phenyl)-4-trifluoromethyl-2-pyridone (Compound 4, Table I) except that the reaction was heated at 80° C. for sixteen hours. The compound showed mp: 168°–169° C.; $\delta$ ($d_6$-acetone) 8.0 (1H,s), 7.8 (1H, dm), 7.0 (1H,m), 6.7 (1H,dd), 2.9 (3H,m).

(ii) 1-(2,6-dichloro-3-ethyl-4-trifluoromethylphenyl)-4-trifluoromethyl-2-pyridone (Compound 5, Table I) except that the reaction was heated at 90° C. for sixteen hours. The compound showed mp 145°–146° C.; $\delta$ ($d_6$-acetone) 8.0 (1H,s), 7.8 (1H, dm), 7.0 (1H,m), 6.7 (1H,dd), 3.0 (2H,q), 1.24 (2H,t).

(iii) 1-(2,3,5,6-tetrafluoro-4-trifluoromethylphenyl)-4-trifluoromethyl-2-pyridone (Compound 7, Table I) except that the reaction was heated at 60° C. for five hours. The compound showed mp 102.6°–103.3° C.; $\delta$ ($d_6$-acetone) 8.05 (1H,d), 7.15 (1H,m) 6.05 (1H,dd).

(iv) 1-(2,3,4,5,6-pentafluorophenyl)-4-trifluoromethyl-2-pyridone (Compound 8, Table I) except that the reaction was heated at 60° C. for five hours. The compound showed $\delta$ ($d_6$-acetone) 7.95 (1H, dm), 7.0 (1H,m), 6.65 (1H,dd).

(v) 1-(2,6-difluoro-4-trifluoromethylphenyl)-4-tertbutyl-2-pyridone (Compound 11, Table I) except that the reaction was heated at 50° C. for three hours. The compound showed mp 152.7°–153.0° C.; $\delta$ ($d_6$ acetone/$CD_3CN$) 7.6 (2H,d), 7.3 (1H,d), 6.5 (2H,M), 1.3 (9H,s).

EXAMPLE 7

This example illustrates the preparation of 1-(2,5,6,-trifluoro-3-methoxy-4-trifluoromethylphenyl-4-trifluoromethyl-2-pyridone (Compound 6, Table 1).

1-(2,3,5,6-tetrafluoro-4-trifluoromethyl phenyl)-4-trifluoromethyl-2-pyridone (Compound 7, 300 mg, 0.79 mmol) was added to a solution made by adding sodium metal (20 mg 0.87 mmol) to methanol (10 ml). When the mixture had been stirred at room temperature for five hours the methanol was evaporated in vacuo, the residue taken up in ethyl acetate, washed with water, dried over magnesium sulphate and evaporated in vacuo to give a yellow oil. The oil was purified by chromatography on silica with 20% diethylether/petrol mixture as eluent to give the requisite compound (140 mg); $\delta$ ($d_6$-acetone) 7.9 (1H,d), 7.0 (1H,m) 6.62 (1H,dd), 4.08 (3H,d).

EXAMPLE 8

The following compounds were prepared by the method described in Example 7 from the appropriate compound of formula I:

(i) 1-(2-fluoro-6-methoxy-4-trifluoromethylphenyl-2-pyridone (Compound 9, Table I) except that the reaction was stirred at 20° C. for three hours and 50° C. for a further three hours. The compound showed mp 140.0°–140.7° C., $\delta$ ($d_6$-acetone 7.9 (1H, d) 7.50 (1H,s), 7.45 (1H,d), 7.00 (1H,m), 6.68 (1H,dd), 4.15 (3H,s).

(ii) 1-(2-chloro-6-methyl-4-trifluoromethyl-phenyl)-4-trifluoromethyl-2-pyridone (Compound 10, Table I) except that the reaction was heated under reflux for eight hours. The compound showed mp 146.6°–147.1° C.; $\delta$ ($d_6$-acetone) 7.93 (1H,d), 7.75 (1H,d), 7.6 (1H,s), 7.59 (1H,s) 6.60 (1H,dd), 4.00 (3H,s).

EXAMPLE 9

This Example illustrates the preparation of 1-(2,6-dichloro-4-trifluoromethylphenyl)-4-difluoromethyl-2-pyridone (Compound 12, Table I).

A dry flask was flushed with nitrogen and charged with 1-(2,6-dichloro-4-trifluoromethyl-phenyl)-4-formyl-2-pyridone (530 mg 1.57 mmol) which had been prepared as described in Example 2. The flask was cooled to 0° C. in an ice bath and diethylaminosulphur trifluoride (DAST) (0.19 ml, 1.57 mmol) was added slowly dropwise. The cooling bath was removed and the reaction mixture stirred at ambient temperature for two hours before being slowly poured into saturated aqueous sodium bicarbonate.

The aqueous mixture was extracted with ethyl acetate and the organic layers washed with water, dried over magnesium sulphate and evaporated in vacuo to give a black gum which was chromatographed on silica with 20% diethylether/petrol mixture as eluant to give the required compound (236 mg, mp 136.5°–137.2° C.); δ ($d_6$-acetone) 8.1 (2H,s), 7.7 (1H,d) 6.9 (1H,t) 6.8 (1H,m), 6.6 (1H,dd).

EXAMPLE 10

This Example illustrates the preparation of Compound 17 in Table I.

Step A

5-Bromo-4-trifluoromethyl-2-pyridone (25 g) was added portionwise to a suspension of sodium hydride (5.5 g of a 50% suspension in mineral oil) in tetrahydrofuran (250 ml) whereupon hydrogen was evolved. The reaction mixture was cooled to −78° C. and a solution (90 ml) of tertiary-butyl lithium (2.6M) in pentane added whilst maintaining the temperature below −55° C. A solution of dry dimethylformamide (40 ml) in tetrahydrofuran (150 ml) at a temperature of −78° C. was added and a thick grey/purple mixture formed. A small amount (ca: 5 mls) ammonium chloride solution was then added and the mixture allowed to warm to room temperature. The resulent yellow solution was partitioned between ammonium chloride (50 ml) and ethylacetate and the ethylacetate extracts were discarded. The aqueous layer was acidified to pH6 using concentrated hydrochloric acid and extracted into ethyl acetate which was washed and dried as described above. The ethyl acetate was then removed under reduced pressure and the resultant brown solid was recrystallised from ethyl acetate to give 5 formyl-4-trifluoromethyl-2-pyridone (13.3 g).

This compound was reacted with 3,5-dichloro-4-fluorobenzotrifluoride described in Example 1 to give Compound A which was found to be 1-(2,6-chloro-4-trifluoromethylphenyl)-5-formyl-5-formyl-4-trifluoromethyl-2-pyridone.

M.P.: 186.9°–188.1° C.

NMR δ ($CDCl_3$): 9.95 (1H, q); 8.0 (1H, d); 7.8 (2H, s); 7.05 (1H, s).

Step B

Compound A (97 mg) prepared as described above was dissolved in ethanol (3 ml) and water (1 ml) and 2M NaOH solution (2 ml) added. To this mixture was added an excess of O-ethyl hydroxylamine hydrochloride in the form of an aqueous solution and the pH of the resultant solution adjusted to 8-9 by the addition of potassium hydroxide pellets with stirring at room temperature. The reaction mixture was heated under reflux for 2 hours and then poured into water, extracted into ether, dried over magnesium sulphate and concentrated under reduced pressure. The product was purified by column chromatography using 30% dietyl ether/petrol as a diluent to give Compound 17 as a white solid (87 mg).

NMR δ ($CDCl_3$): 8.55 (s, 1H); 8.10 (s, 1H); 7.79 (s, 2H); 7.35 (s, 1H); 7.10 (m, 1H); 7.06 (s, 1h); 4.1–4.3 (m, 2H); 1.3–1.4 (m, 3H).

EXAMPLE 11

The following compounds were prepared in an analogous manner to that described in Example 10.

| Compound 18 | NMR δ ($CDCl_3$) | 8.52 (1H, s); 7.72 (2H, s); 7.40 (1H, m); 7.28 (5H, s); 7.10 (1H, s); 5.10 (2H, s). |
|---|---|---|
| Compound 19 | NMR δ ($CDCl_3$) | 8.24 (2H, d); 8.2 (1H, s); 7.79 (2H, s); 7.71 (1H, s); 7.5 (2H, d); 7.07 (1H, s); 5.24 (2H, s). |
| Compound 20 | NMR δ ($CDCl_3$) | 8.48 (1H, s); 8.10 (1H, m); 7.88 (2H, s); 7.80 (2H, s); 7.76 (1H, s); 7.30 (1H, m); 7.05 (1H, s); 3.98 (3H, s); 3.92 (3H, s). |
| Compound 21 | NMR δ ($CDCl_3$) | 8.46 (1H, s); 7.9 (1H, s); 7.8 (2H, s); 7.30 (2H, dd); 7.15 (2H, dd); 7.11 (1H, s); 7.05 (1H, dt). |
| Compound 22 | NMR δ ($CDCl_3$) | 8.08 (1H, s); 7.81 (2H, s); 7.69 (1H, s); 7.06 (1H, s); 1.31 (9H, s). |
| Compound 23 | NMR δ ($CDCl_3$) | 8.15 (1H, s); 7.79 (2H, s); 7.72 (1H, s); 7.06 (1H, s); 6.00 91H, ddt); 5.29 (1H, dd); 5.23 (1H, dd); 4.63 (2H, d). |
| Compound 24 | NMR δ ($CDCl_3$) | 8.10 (1H, s); 7.80 (2H, s); 7.71 (1H, s); 7.05 (1H, s); 5.21 (2H, s). |

EXAMPLE 12

This Example illustrates the preparation of Compound 15 in Table I.

A solution of 5-bromo-4-trifluoromethyl-2-pyridone (1 g) in tetrahydrofuran (10 ml) was added to a suspension of sodium hydride (0.22 g of a 50% suspension in mineral oil) in tetrahydrofuran (10 ml) whereupon hydrogen was evolved. The mixture was cooled to −75° C. and a 7.7M solution of t-butyllithium in pentane (5.35 ml) was added dropwise, keeping the temperature below −60° C. $CF_3SCl$ gas was condensed into a flask at −78° C. and then distilled into the reaction vessel through a canula. A slightly exothermic reaction took place to give a red solution. A few drops of ammonium chloride solution were then added to quench the reaction mixture which was then allowed to warm up to room temperature. The reaction mixture was partitioned between aqueous ammonium chloride and ethylacetate. The organic extracts were washed with brine, dried over magnesium sulphate and the ethyl acetate removed under reduced pressure. The remaining orange crystals were recrystallised using ethyl acetate, and the product reacted with 3,5-dichloro-4-fluorobenzotrifluoride as described in Example 1 to give Compound 15 as white crystals.

NMR δ ($CDCl_3$): 7.8 (2H, s); 7.6 (1H, s); 7.1 (1H, s).

EXAMPLE 13

This Example illustrates the preparation of Compound 25 in Table I.

A solution of 5-bromo-4-trifluoromethyl-2-pyridone (1.7 g) in tetrahydrofuran (30 ml) was added slowly to a suspension of sodium hydride (0.37 g of a 50% suspension in mineral oil) in tetrahydrofuran and the solution cooled to −85° C. A 1.56M solution of t-butyllithium in pentane (9.9 ml) was added whilst maintaining the temperature below −80° C. Methyl iodide (5 eq) was then added to the mixture which resulted in an exothermic reaction which raised the temperature to −30° C. After stirring for 10 minutes, water was added to the reaction mixture at −50° C. and the pH adjusted to 4 by the addition of aqueous hydrochloric acid. The aqueous reaction mixture was extracted into trichloromethane and the extracts washed with brine and dried over magnesium sulphate. Trichloromethane was removed under reduced pressure and the remaining solid recrystallized from a mixture of ethyl acetate and petrol. The product (780 mg) was reacted with 3,5-dichloro-4-fluorobenzotrifluoride as described in Example 1 to give Compound 25.

NMR δ (CDCl$_3$): 7.8 (2H, s); 7.05 (1H, s); 6.9 (1H, s); 2.1 (3H, t).

Compounds 14, 16 and 28 were prepared in an analogous manner using ICN, n-butylbromide and CH$_3$S-SCH$_3$ respectively in place of methyl iodide in the Example 13.

| Compound 14 | M.P. 134.6–135.7° C. NMR δ (acetone) | 8.3 (1H, s); 8.1 (2H, s); 7.1 (1H, s). |
|---|---|---|
| Compound 16 | NMR δ (CDCl$_3$) | 7.8 (2H, s); 7.0 (1H, s); 6.9 (1H, s); 2.55 (2H, m); 1.5 (4H, m; 0.95 (3H, m). |
| Compound 24 | M.P. 115.0–116.4° C. NMR δ (acetone) | 8.1 (2H, m); 8.05 (1H, m); 7.05 (1H, m); 2.4 (3H, s). |

EXAMPLE 14

This Example illustrates the preparation of Compound 26 in Table I.

Compound 15 (100 mg) prepared as described in Example 12 was dissolved in dry dichloromethane (2 ml), metachloroperbenzoic acid (43 mg) was added portionwise and the mixture heated under reflux for 4 hours. The mixture was then run through a silica column using 10% diethyl ether in petrol as eluent. Compound 26 was recovered as a white solid (80 mg).

NMR δ (CDCl$_3$): 8.05 (1H, s); 7.8 (2H, s); 7.1 (1H, s).

EXAMPLE 15

This Example illustrates the preparation of Compound 27 in Table I.

Compound A (0.5 g) prepared as described in Example 10, Step A was dissolved in dichloromethane (3 ml) and added to a suspension of triphenyl phosphine (0.65 g), zinc (0.16 g) and carbon tetrachloride (0.38 g) in dichloromethane (2 ml). The mixture was heated under reflux for 4 hours then added to water and extracted into diethyl ether. The extracts were washed with brine, dried over magnesium sulphate and the diethyl ether removed under reduced pressure. The remaining buff coloured solid was run through a silica column using 10% diethyl ether/petrol as eluent and Compound 27 recovered as a white solid (345 mg).

NMR δ (CDCl$_3$(: 7.8 (2H, s); 7.4 (1H, m); 7.1 (1H, m); 6.7 (1H, m).

EXAMPLE 16

This Example illustrates the preparation of Compound 29 in Table I.

Compound A (0.5 g) was prepared as described in Example 10 Step A, mixed with hydroxylamine hydrochloride (0.095 g), sodium formate (0.095 g) and 98% formic acid (2 ml) and the mixture was heated under reflux for 4 hours. The aqueous mixture was then extracted into diethyl ether and the extracts washed with aqueous sodium bicarbonate solution followed by brine and dried over magnesium sulphate. The diethyl ether was removed under reduced pressure leaving a white solid which was purified by column chromatography on a silica column using 20% diethyl ether/petrol to give Compound 29 as a white solid (130 mg).

NMR δ (CDCl$_3$): 7.8 (2H, s); 7.75 (1H, s); 7.1 (1H, s).

1-(2,6-Dibromo-4- trifluoromethylphenyl)-5-formyl-4-trifluoromethyl-2-pyridone (Compound B) was prepared in a manner analogous to that described in Example 10 Step A but using 3,5-dibromo-4-fluorobenzotrifluoride in the final condensation reaction.

Compound 30 was prepared from Compound B in an analogous manner to that described above for the preparation of Compound 29 from Compound A.

NMR δ (CDCl$_3$): 8.0 (2H, s); 7.7 (1H, s); 7.1 (1H, s).

EXAMPLE 17

This Example illustrates the preparation of Compound 31 in Table I.

4-Trifluoromethyl-2-pyridone (20 g) was dissolved in concentrated sulphuric acid (100 ml) and the mixture warmed to 35° C. A nitrating mixture comprising concentrated nitric acid (11.1 g) and sulphuric acid (10 ml) was added in stages and the mixture warmed to 65° C. for a total of 1½ hours. After this the mixture was poured into ice and a white precipitate formed which was filtered off and the aqueous phase extracted into ethyl acetate and the extracts washed with brine and dried over magnesium sulphate. The solvent was removed under reduced pressure to give a brown oil. This oil was run through a silica column using 5% methanol in dichloromethane as eluent and 5-nitro-4-trifluoromethyl-2-pyridone was collected as a white solid. This was reacted with 3,5-dichloro-4-fluorobenzotrifluoride as described in Example 1 to give Compound 31 as a yellow solid.

M.P.: 144.2°–144.8° C.

NMR δ (CDCl$_3$): 8.4 (1H, s); 7.8 (2H, s); 7.5 (1H, s).

EXAMPLE 18

This Example illustrates the preparation of Compound 32 in Table I.

Compound A (1 g) prepared as described in Example 10 Step A was suspended in methanol (10 ml), sodium borohydride (94 mg) was added and the reaction mixture stirred at room temperature until all the aldehyde (A) had been consumed (TLC: 30% ethylether/petrol eluent).

A yellow precipitate was formed. The reaction mixture was added to brine (100 ml) and extracted into ethyl acetate. The extracts were washed with brine, dried over magnesium sulphate and the solvent removed under reduced pressure to give Compound 32 as an off white solid.

NMR δ (CDCl$_3$): 7.7 (2M, s); 7.33 (1H, s); 7.04 (1H, s); 4.67 (2H, s); 2.24 (1H, br, s).

EXAMPLE 19

This Example illustrates the preparation of Compound 33 in Table I.

Compound 32 (350 mg) was mixed with triphenyl phosphine (250 mg) and carbon tetrachloride (6 ml) and the mixture heated under reflux for 10 hours after which the reaction mixture was added to water and then extracted into diethyl ether. The extracts were washed with brine, dried over magnesium sulphate and the solvent removed under reduced pressure. The resultant off-white solid was run through a silica column using 20% diethyl ether in petrol as eluent and Compound 33 obtained as a white solid (200 mg).

NMR δ (CDCl$_3$): 7.8 (2H, s); 7.35 (1H, s); 7.1 (1H, s); 4.55 (2H, s).

EXAMPLE 20

This Example illustrates the preparation of Compound 34 in Table I.

A Wittig reagent was prepared by suspending Ph$_3$P+CH$_2$Cl Cl$^-$ (0.43 g) in dry tetrahydrofuran (10 ml) cooling to −78° C. and adding potassium t-butoxide (0.30 g) portionwise.

Compound A (0.5 g) (as described in Example 10 Step A) was dissolved in tetrahydrofuran (5 ml) and the solution cooled to −78° C.

The Witting reagent was then added to the solution which was stirred for ½ hour and then allowed to warm to room temperature. The mixture was added to water, extracted into diethyl ether and the extracts washed with brine and dried over magnesium sulphate. After removal of solvent under reduced pressure, the remaining solid was passed down a silica column using 5% diethyl ether in petrol as eluent and the fractions collected. Compound 34 was obtained by recrystallisation of the product from 60-80 petrol as a white solid.

NMR δ (CDCl$_3$): 7.8 (2H, s); 7.4 (1H, s); 3.0 (1H, m); 3.2 (1H, s).

EXAMPLE 21

This Example illustrates the preparation of Compound 35 in Table I. DAST (0.17 ml) was added to solid Compound A (0.5 g) at 0° C. and the mixture stirred for one hour. A further sample of DAST (1 ml) was added and the mixture stirred for two days. It was then diluted with dichloromethane (ca. 3 ml) and added slowly to aqueous sodium bicarbonate solution. A vigorous reaction occurred with effervescence. The aqueous phase was extracted into dichloromethane, the extracts washed with brine and dried over magnesium sulphate and the solvent removed under reduced pressure. Purification by chromatography using a silica column and 20% diethyl ether/petrol as eluent yielded Compound 35 as a white solid.

M.P.: 132.0°−132.8° C.

NMR δ (CDCl$_3$): 7.8 (2H, s); 7.6 (1H, s); 7.1 (1H, s); 6.7 (1H, t).

EXAMPLE 22

This Example illustrates the preparation of Compound 36 in Table I.

Compound A (0.5 g), (described in Example 10 Step A) phosphorus pentachloride (0.28 g) and carbon tetrachloride (3 ml) were refluxed together for one hour. The reaction mixture was then added to water, extracted into ethyl acetate and the ethyl acetate extracts washed first with sodium bicarbonate and then with brine. After drying over magnesium sulphate the solvent was removed under reduced pressure and the resultant solid purified by running through a silica column using 20% diethyl ether/petrol as eluent. Compound 36 was obtained as a white solid (460 mg).

M.P.: 112°−114° C.

NMR δ (CDCl$_3$): 7.9 (1H, s); 7.8 (2H, s); 7.0 (1H, s); 6.8 (1H, s).

EXAMPLE 23

This Example illustrates the preparation of Compound 37 in Table I.

The Wittig salt Ph$_3$P+CH$_2$CN Cl$^-$ (0.46 g) was suspended in tetrahydrofuran, cooled to −78° C., and potassium t-butoxide (0.153 g) added portionwise. After ensuring complete formation of the anion by allowing the solution to warm to room temperature and stirring for half an hour, the solution was cooled to −78° C. and added to a solution of Compound A (0.5 g) in tetrahydrofuran (3 ml) also at −78° C. The mixture was allowed to warm to room temperature, stirred for one hour and added to water. The mixture was extracted into diethyl ether and the extracts washed with brine, and dried over magnesium sulphate. The diethyl ether was removed under reduced pressure and the resulting oil run through a silica column using a 20% diethyl ether/petrol as eluent.

Compound 37 was recovered as a white solid (340 mg).

NMR δ (CDCl$_3$): 7.9 (1H, s); 7.8 (2H, s); 7.2 (1H, d); 7.1 (1H, s); 5.6 (1H, d).

EXAMPLE 24

This Example illustrates the preparation of Compound 39 in Table I.

Step A

Sodium hydride suspension (0.36 g, of a 50% suspension in mineral oil) was washed with 40/60 petrol under nitrogen to remove the oil. A solution of 4-trifluoromethyl-2-pyridone (1.1 g) dissolved in dry dimethylformamide (10 ml) was added dropwise. The reaction mixture was stirred at room temperature, under nitrogen for ½ hour. After this time 3,5-dichloro-4-fluoro-nitrobenzene (2.0 g) dissolved in dry dimethylformamide (5 ml) was added in one portion. The reaction mixture was heated at 100° C. for 4½ hours, then the reaction temperature was increased to 110° C. for a further c.a. 20 hours. After this time, the reaction was cooled and quenched with water. The mixture was acidified with dilute hydrochloric acid and extracted with ethyl acetate (2×50 ml). The combined organic extracts were washed with brine (3×30 mls) and dried over magnesium sulphate. The organic layer was then concentrated under reduced pressure to give a yellow solid. The compound was passed down a silica column using 4:1 petrol/ether as the eluting solvent, the compound being eluted very slowly. The fractions containing the product were confirmed and the solvent removed under reduced pressure. The residue was triturated with pentane and collected by filtration under reduced pressure. 1-([2,6-dichloro-4-nitro)phenyl]-4-trifluoroemthyl-2-pyridone was obtained as a white crystalline solid (1.18 g).

NMR δ (CDCl$_3$): 8.53 (2H, s); 7.81 (1H, d); 6.98 (1H, m); 6.70 (1H, dd).

Step B

A sample of the product of Step A (0.5 g) was suspended in methanol (5 ml).

The suspension was added dropwise to a stirred solution of stannous chloride (0.81 g) in concentrated hydrochloric acid (1.3 ml) at room temperature. A slightly exothermic reaction was noted after which the reaction mixture was stirred at room temperature for 1 hour, and allowed to stand overnight at room temperature. The mixture was quenched with water, basified and extracted with ethyl acetate (2×25 ml). The organic layers were combined and washed with brine (3×30 ml). The acid layer was then basified with 10M aqueous sodium hydroxide solution in the presence of ethyl acetate (30 ml) and the aqueous layer was extracted twice with ethyl acetate (2×30 ml). The combined organic layers were dried over magnesium sulphate and the solvent removed under reduced pressure to give Compound 38 as a yellow crystalline solid.

IR (nujol): 3500 cm$^{-1}$, 3350 cm$^{-1}$ and 1682 cm$^{-1}$.

EXAMPLE 25

This Example illustrates the preparation of Compound 39 in Table I.

Concentrated hydrochloric acid (0.47 ml) and water (0.47 ml) were added together to Compound 38 (600 mg) with constant stirring and the mixture cooled to 0° C. in an ice/salt bath. A solution of sodium nitrite (133 mg) in water (0.3 ml) was added with stirring whilst maintaining the temperature below 5° C.

A cuprous chloride solution was prepared by dissolving copper sulphate (6.25 g) and sodium chloride (1.625 g) in water (20 ml) and mixing 1.1 mls of this solution with 2.2 mls of a solution prepared from sodium bisulphate (2.65 g), sodium hydroxide (1.75 g) and water (20 ml).

The cuprous chloride solution (3.3 ml) was added slowly to the reaction mixture and small amounts of water added to wash solid material from the sides of the flask. The mixture was allowed to warm up to room temperature and then water added, followed by a basifying amount of sodium bicarbonate solution. The solution was extracted into ethyl acetate (2×30 ml) and the combined organic extracts washed with water/brine, dried over magnesium sulphate and concentrated under reduced pressure to give a yellow oil. This oil was dissolved in trichloromethane, preabsorbed onto silica gel under reduced pressure and passed down a silica column using 50/50 petrol/ether as eluent. Compound 39 was isolated from the first two fractions by removing solvent under reduced pressure and recrystallising the product from a mixture of pentane and ether.

NMR δ (CDCl$_3$): 7.53 (2H, s); 7.18 (1H, d); 6.97 (1H, m); 6.42 (1H, dd).

EXAMPLE 26

This Example illustrates the preparation of Compound 40 in Table I.

Step A

This describes the preparation of 4-trifluoromethyl-1-(2,6-dichloro-4-ethoxycarbonylphenyl)-b 2-pyridone (Compound C). 3,5-Dichloro-4-fluorobenzotrifluoride (35 g, 0.15 mol) was slowly added to concentrated sulphuric acid (120 ml) with stirring. The mixture was heated to 100° C. for 24 hours.

The reaction mixture was slowly poured onto ice (500 g) and the white solid which was formed was filtered off. The solid was dissolved in dilute NaOH (2N) and the solution filtered before treating with concentrated HCl to pH=1. A thick white precipitate was produced which was filtered. The solid was dissolved in ether (300 ml) and the remaining water separated. The organic layer was dried over magnesium sulphate and evaporated in vacuo to give a white solid, 3,5-dichloro-4-fluorobenzoic acid (27.6 g).

Melting Point: 194.5°–195.0° C.

NMR δ (CDCl$_3$, d$_5$ DMSO): 8.0 (2H, d).

Potassium carbonate (36 g, 0.26 moles) was added to a stirred mixture of 3,5-dichloro-4-fluorobenzoic acid (27.6 g, 0.13 moles), ethyl iodide (41.2 g–0.26 moles) and dry dimethylformamide (300 ml) under nitrogen. The reaction was heated to 80° C. for 6 hours. The dimethylformamide was removed in vacuo and the residue treated with water (200 ml) acidified with dilute hydrochloric acid and extracted with ethylacetate (2×250 ml). The organic layer was washed with water, dried over magnesium sulphate and evaporated in vacuo, to give an orange oil which was purified by chromatography on silica, using a 4:1 mixture of petrol and diethylether as eluent. The pink oil obtained crystallised on standing, and washing with ice-cold 40–60 petrol gave white crystals of ethyl 3,5-dichloro-4-fluorobenzoate (29 g).

Melting Point: 59.5°–60.0° C.

NMR δ (CDCl$_3$): 1.40 (3H, t), 4.36 (2H, q); 8.00 (2H, d).

Sodium hydride (5.28 g of a 50% dispersion in mineral oil, 0.11 mol) was washed with diethylether in a dry flask flushed with nitrogen. Dry dimethylformamide (150 ml) was added and the mixture gently stirred at room temperature, whilst 4-trifluoromethyl-1-pyridone (16.3 g, 0.1 mol) was added portionwise.

After 15 minutes, when the gas evaluation had ceased, ethyl 3,5-dichloro-4-fluorobenzoate (29.0 g, 0.12 mol) was added, and the reaction was heated to 90° C. for 20 hours.

The dimethylformamide was removed in vacuo and the residue treated with water (100 ml) and dilute HCl and extracted with ethylacetate (2×100 ml). The combined organic portions were washed with water, dried over magnesium sulphate and evaporated in vacuo. The residue was washed with an diethylether/petrol mixture to give a white solid which was purified further by recrystallization from a mixture of diethylether and petrol to give white crystals of 4-trifluoromethyl 1-(2,6-dichloro-4-ethoxycarbonylphenyl)-2-pyridone (Compound C) (21.6 g).

Melting Point: 126.7°–127.8° C.

NMR δ (d$^6$ acetone): 1.40 (3H, t), 4.40 (2H, q), 6.65 (1H, dd), 6.97 (1H, m), 7.80 (1H, d, m), 8.20 (2H, s).

Step B

This describes the preparation of 4-trifluoromethyl-1-(2,6-dichloro-4-formylphenyl)-2-pyridone (Compound E).

A solution of potassium hydroxide [51 g (1.1 mol) in 50 ml of water] was added to a stirred solution of 4-trifluoromethyl-1-(2,6-dichloro-4-ethoxycarbonylphenyl)-2-pyridone (Compound C) in ethanol [35 g (0.09 mol) in 500 ml of ethanol]. The reaction was stirred for one hour at room temperature. The ethanol mixture was removed in vacuo and the residue treated with dilute HCl and extracted with ethylacetate (2×300 ml). The combined organic portions, were washed well with water, dried over magnesium sulphate and evaporated in vacuo to give a white solid of 4-trifluoromethyl-1-(2,6-dichloro-4-carboxyphenyl)-2-pyridone (31.3 g).

Melting Point: 259°–260° C.

NMR δ (d⁶ acetone): 6.62 (1H, dd), 6.83 (1H, m), 7.76 (1H, d, m), 8.10 (2H, s).

Borane (56 ml of a 1M solution in tetrahydrofuran (57 mmol) was added dropwise to an ice cooled solution of 4-trifluoromethyl-1-(2,6-dichloro-4-carboxyphenyl)-2-pyridone (10 g, 28 mmol) in dry tetrahydrofuran (100 ml) under nitrogen. When the addition was complete the reaction was stirred at 0° C. for 30 minutes, before allowing it to slowly warm up to room temperature, and continue stirring for 5 hours. It was left to stand at room temperature overnight.

The reaction was thrown into a mixture of water (100 ml) and saturated sodium bicarbonate solution (50 ml) and extracted with ethylacetate (2×100 ml). The combined organic extracts were washed with saturated bicarbonate solution and water, dried over magnesium sulphate and evaporated in vacuo to leave a colourless oil, which solidified on standing. Recrystallization from a mixture of petrol and ethylacetate gave 4-trifluoromethyl-1-(2,6-dichloro-4-hydroxymethylphenyl)-2-pyridone (Compound D) (6.7 g).

Melting Point: 151.0°–151.5° C.

NMR δ (d⁶ acetone): 4.67 (2H, s), 6.52 (1 H, dd), 6.88 (1H, m), 7.54 (2H, s), 7.66 (1H, d, m).

Dry dimethylsulphoxide in dry dichloromethane [1.25 ml (18 mmol) of DMSO in 4 ml of CH₂Cl₂] was added dropwise to a well stirred solution of oxalylchloride in dry dichloromethane (1.03 g of oxalylchloride (8.1 mmol) in 20 ml of CH₂Cl₂) at −60° C. in a flask that had been purged with nitrogen. When the addition was complete the reaction was stirred at −60° C. for ten minutes. The 4-trifluoromethyl-1-(2,6-dichloro-4-hydroxyphenyl)-2-pyridone (Compound D) (2.5 g, 7.4 mmol) in dry dichloromethane (5 ml) was added slowly dropwise at −60° C., and then stirred for 15 minutes. The triethylamine (5 ml, 37 mmol) was added dropwise, and after stirring at −60° C. for another 10 minutes the reaction was slowly warmed up to room temperature.

The reaction was thrown into water (50 ml) and extracted with dichloromethane (2×100 ml). The combined organic portions were washed with saturated sodium bicarbonate solution and then water, dried over magnesium sulphate and evaporated in vacuo to give a yellow solid which was purified by chromatography on silica using a 2:1 mixture of petrol and ethylacetate as eluent, to give 4-trifluoromethyl-1-(2,6-dichloro-4-formylphenyl)-2-pyridone (Compound E) (1.5 g).

Melting Point: 152.4°–153.5° C.

NMR δ (d⁶ acetone): 6.70 (1H, dd), 7.00 (1H, m), 7.82 (1H, d, m), 8.16 (2H, s), 10.10 (1H, s).

Step C

A dry flask was flushed with nitrogen and charged with 4-trifluoromethyl-1-(2,6-dichloro-4-hydroxymethylphenyl)-2-pyridone (Compound D) [0.73 g (2.2 mmol)] and dry dichloro-methane (15 ml). The flask was cooled to −78° C. and diethylaminosulphurtrifluoride (0.31 ml, 2.4 mmol) was added slowly dropwise. The reaction was stirred at −78° C. for 2 hours and then slowly allowed to warm up to room temperature. The reaction was slowly added to a saturated solution of sodium hydrogen carbonate (20 ml) and extracted with ethyl acetate (2×30 ml). The combined organic layers were washed well with water, dried over magnesium sulphate, and evaporated in vacuo to give a yellow solid which was chromatographed on silica with 50% petrol/diethyl ether as eluent. Recrystallisation from a mixture of pentane and diethylether gave 4-trifluoromethyl-1-(2,6-dichloro-4-fluoromethylphenyl)-2-pyridone (Compound 40) (0.18 g)

Melting Point: 121.4°–122.0° C.).

NMR δ (d⁶ acetone): 5.36 (2H, s), 6.62 (1H, dd), 6.92 (1H, m), 7.70 (2H, m), 7.80 (1H, d, m).

EXAMPLE 27

This Example illustrates the preparation of Compound 13 in Table I.

4-Trifluoromethyl-1-(2,6-dichloro-4-difluoromethylphenyl)-2-pyridone (Compound 13) was prepared from Compound E as described in Example 26 by the method described in Example 26 (Step C) except the reaction was carried out at 0° C. When the addition of diethylaminosulphurtrifluoride was complete the reaction was stirred at 0° C. for 1½ hours. Recrystallization from petrol (40°–60° C. boiling range) gave the required Compound 13.

Melting Point: 125.3°–126.0° C.

NMR δ (CDCl₃): 6.04, 6.66, 7.28 (1H, t), 6.44 (1H, dd), 7.00 (1H, m), 7.20 (1H, d, m), 7.68 (2H, s).

EXAMPLE 28

This Example illustrates the preparation of 4-trifluoromethyl-1-(2,6-dichloro-4-dichloromethylphenyl)-2-pyridone (Compound 14 in Table I).

4-Trifluoromethyl-1-(2,6-dichloro-4-formylphenyl)-2-pyridone (Compound E from Example 26) (1 g, 3 mmol) was added portionwise to a well stirred solution of phosphorous pentachloride (0.68 g, 3.3 mmol) in carbon tetrachloride (10 ml) at room temperature in a flask that had been purged with nitrogen. The reaction was stirred for 2½ hours and then left to stand overnight. Additional phosphorous pentachloride was added, and stirring continued for another 6 hours until all the starting material had been consumed.

The reaction was slowly added to a saturated solution of sodium bicarbonate (30 ml) and extracted with ethylacetate (2×30 ml). The combined organic portions were washed with saturated bicarbonate solution and water, dried over magnesium sulphate and evaporated to give an off white solid. Chromatography on silica using a 2:1 mixture of petrol and diethylether was eluent, followed by recrystallization from a mixture of diethylether and pentane gave 4-trifluoromethyl-1-(2,6-dichloro-4-dichloromethylphenyl)-2pyridone (Compound 14) (0.35 g).

Melting Point: 175.9°–176.8° C.

NMR δ (d⁶ acetone): 6.68 (1H, dd), 6.96 (1H, m), 7.30 (1H, s), 7.82 (1H, d, m), 7.98 (2 H, s).

EXAMPLE 29

This Example illustrates the preparation of 4-trifluoromethyl-1-(2,6-dichloro-4-(1'-fluoro-1'-methylethylphenyl)-2-pyridone (Compound 41 in Table I).

A dry flask was flushed with nitrogen and charged with magnesium (0.42 g, 17 mmol), dry ether (10 ml) and a crystal of iodine. 1 ml of a solution of methyliodide (2.5 g of methyliodide in 20 ml of dry ether) was added and when the iodine was decolourised the remainder was added dropwise. The reaction was stirred at room temperature for 1 hour, and then the 4-trifluoromethyl-1-(2,6-dichloro-4-ethoxycarbonylphenyl)-

2-pyridone (Compound C) (3 g, 7.9 mmol) in dry ether (40 mll) was added dropwise. The reaction was stirred for 1 hour at room temperature and was then thrown into water (50 ml), acidified with dilute hydrochloric acid, and extracted with ethylacetate (2×40 ml). The combined organic extracts were washed well with water and brine, dried over magnesium sulphate and evaporated in vacuo to give a yellow oily solid. Chromatography on silica, with 50% petrol/diethylether as eluent, followed by recrystallisation from a mixture of ethylacetate and petrol (60°–80° C. boiling range) gave 4-trifluoromethyl-1-(2,6-dichloro-4-(1'-hydroxy-1'-methylethylphenyl)-2-pyridone (1.6 g).

Melting Point: 149.4°–150.5° C.

NMR δ (d⁶ acetone): 1.6 (6H, s), 4.56 (1H, s), 6.60 (1H, dd), 6.92 (1H, m), 7.76 (1H, d, m), 7.76 (2H, s).

4-Trifluoromethyl-1-(2,6-dichloro-4-(1'-hydroxy-1'-methylethylphenyl)-2-pyridone was treated with diethylaminosulphurtrifluoride as described in Example 26 (Step C). Recrystallisation from a mixture of petrol (40°–60° C. boiling range) and diethylether gave a white compound, 4-trifluoromethyl-1-(2,6-dichloro-4-(2'-fluoro-2'-methylethylphenyl)-2-pyridone (Compound 41) (0.4 g).

Melting Point: 173.6°–174.9° C.

NMR δ (d⁶ acetone): 1.76 (6H, d), 6.60 (1H, dd), 6.94 (1H, m), 7.72 (2H, s), 7.76 (1H, d, m).

The insecticidal activity of compounds of formula (I) is set out in the following Table II as a grading of A, B or C where A indicates that 80-100% mortality was observed, B indicates that 50-79% mortality was observed and C indicates that 0-49% mortality was observed. The tests were conducted by spraying a suitable support medium (e.g., leaves of a suitable food plant, or filter paper) with a solution of the compound under test and placing the pests thereon. Assessment of mortality was made 72 hours after spraying. In the test the compounds were used in the form of aqueous composition prepared by dissolving the compound in mixture of solvents consisting of 1 part by volume of acetone and 1 part by volume of ethanol and diluting the solution with water containing 1% by volume of a wetting agent (Synperonic "NX-Synperonic" is a Registered Trade Mark).

TABLE II

| COMPOUND | RATE OF APPLICATION ppm | NL | MD | BG | HV | CP | DB |
|---|---|---|---|---|---|---|---|
| 1 | 500 | C | C | C | C | C | C |
| 2 | 500 | C | C | C | C | C | C |
| 3 | 500 | C | C | C | C | C | C |
| 4 | 500 | A | B | C | C | B | C |
| 5 | 500 | C | A | C | C | A | C |
| 6 | 500 | C | C | C | C | C | C |
| 7 | 500 | C | A | B | C | C | C |
| 8 | 500 | C | A | C | A | A | — |
| 9 | 500 | C | B | C | C | C | C |
| 10 | 500 | C | B | C | C | C | C |
| 11 | 500 | A | C | C | C | C | — |
| 12 | 500 | A | C | C | C | C | A |
| 13 | 500 | A | A | C | A | — | A |
| 14 | 500 | A | C | C | C | — | C |
| 16 | 500 | A | B | C | C | — | C |
| 17 | 500 | — | C | A | C | — | C |
| 20 | 500 | C | A | C | C | C | C |
| 25 | 500 | A | A | B | C | — | C |
| 27 | 500 | C | C | B | C | — | C |
| 28 | 500 | A | B | B | B | — | C |
| 29 | 500 | — | A | A | C | — | C |
| 30 | 500 | — | A | C | B | — | C |
| 31 | 500 | — | A | A | C | — | C |
| 33 | 500 | — | C | C | C | — | B |
| 34 | 500 | — | C | A | C | — | C |
| 35 | 500 | — | A | A | C | — | B |
| 36 | 500 | — | B | C | C | — | C |
| 37 | 500 | — | C | C | A | — | A |
| 40 | 500 | B | C | C | C | — | C |
| 41 | 500 | A | B | C | C | — | C |

TABLE III

| CODE LETTERS (Table III) | TEST SPECIES | SUPPORT MEDIUM/FOOD | TYPE OF TEST | DURATION (days) |
|---|---|---|---|---|
| NL | Nilaparvata lugens (brown plant hopper) | Rice plants | CT | 3 |
| CP | Chilo partellus (maize stem bore) | Oil seed rape leaf | RT | 3 |
| DB | Diabrotica balteata (rootworm larvae) | Filter paper/ maize seed | RT | 3 |
| BG | Blattella germanica (cockreach nymphs) | Plastic pot/ calf weenes pellets | RT | 3 |
| MD | Musca domestica (houseflies - adults) | Cotton wool/ sugar | CT | 1 |
| HV | Heliothis virescens | Cotton leaf | RT | 3 |

We claim:
1. A compound of formula (V)

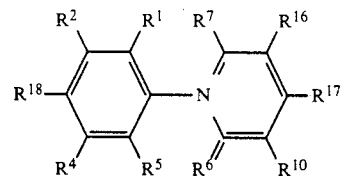

wherein
$R^1$, $R^2$, $R^4$ and $R^5$ are independently selected from hydrogen, halogen, lower alkyl optionally substituted by halogen, lower alkoxy optionally substituted by halogen and lower alkenyl optionally substituted by halogen;
$R^6$ is oxygen or sulphur;
$R^7$ and $R^{10}$ are independently selected from hydrogen, halogen, lower alkyl optionally substituted by halogen, lower alkoxy optionally substituted by halogen, and lower thioalkoxy optionally substituted by halogen;
$R^{16}$ is formyl or $R^{16}$ is hydrogen, halogen, lower alkyl optionally substituted by halogen or hydroxy, lower alkoxy, lower thioalkoxy, cyano, nitro, oximino optionally substituted by lower alkyl, aryl, lower alkenyl or aralkyl wherein the aryl portion is optionally substituted with halogen or nitro; lower alkenyl, optionally substituted by halogen or cyano; $S(O)_nR^{11}$ where n is 0, 1 or 2 and $R^{11}$ is lower alkyl optionally substituted by halogen;

$R^{17}$ is formyl, or $R^{17}$ is hydrogen, or lower alkyl optionally substituted by halogen, lower alkenyl optionally substituted by halogen or $CO_2R^{12}$ wherein $R^{12}$ is lower alkyl optionally substituted by halogen;

$R^{18}$ is nitro, or $C_{1-6}$ alkoxycarbonyl or lower alkyl substituted by hydroxy, or $R^{18}$ is halogen, amino, mono- or di-(lower alkyl)-amino, lower alkyl substituted by halogen, lower alkoxy optionally substituted by halogen and lower alkenyl optionally substituted by halogen, provided that $R^{18}$ is not monochloro- or monobromomethyl; and provided further that $R^{16}$ is formyl or $R^{17}$ is formyl or $R^{18}$ is nitro, or $C_{1-6}$ alkoxycarbonyl or lower alkyl substituted by hydroxy; and that when $R^{18}$ is trifluoromethyl and $R^1$ and $R^5$ are halogen, $R^2$ and $R^4$ are not both hydrogen; and that $R^7$, $R^{16}$, $R^{17}$ and $R^{10}$ do not comprise from one to four halogen or trihalomethyl substituents.

2. A compound of formula (IIIA):

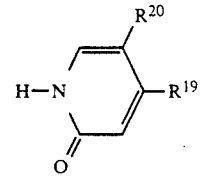

wherein
$R^{19}$ is trihalomethyl and
$R^{20}$ is an electrophilic group selected from nitro, lower thioalkoxy optionally substituted by halogen, formyl, and lower alkyl optionally substituted by halogen.

* * * * *